US008779766B2

(12) United States Patent
Marumoto

(10) Patent No.: US 8,779,766 B2
(45) Date of Patent: Jul. 15, 2014

(54) ELECTRON SPIN MEASUREMENT DEVICE AND MEASUREMENT METHOD

(75) Inventor: Kazuhiro Marumoto, Tsukuba (JP)

(73) Assignee: University of Tsukuba, Ibaraki (JP)

(*) Notice: Subject to any disclaimer, the term of this patent is extended or adjusted under 35 U.S.C. 154(b) by 408 days.

(21) Appl. No.: 13/122,819

(22) PCT Filed: Oct. 2, 2009

(86) PCT No.: PCT/JP2009/005094
§ 371 (c)(1),
(2), (4) Date: Apr. 6, 2011

(87) PCT Pub. No.: WO2010/041393
PCT Pub. Date: Apr. 15, 2010

(65) Prior Publication Data
US 2011/0193559 A1 Aug. 11, 2011

(30) Foreign Application Priority Data

Oct. 6, 2008 (JP) .................................. 2008-259622
Nov. 4, 2008 (JP) .................................. 2008-282823

(51) Int. Cl.
*G01V 3/00* (2006.01)
(52) U.S. Cl.
USPC .......................................... 324/304; 324/300
(58) Field of Classification Search
USPC ......................... 324/300–322; 600/406–445
See application file for complete search history.

(56) References Cited

U.S. PATENT DOCUMENTS 3,969,115 A * 7/1976 Savia ............................ 430/358
5,465,047 A * 11/1995 Nakanishi et al. ............ 324/316
(Continued)

FOREIGN PATENT DOCUMENTS

JP 04-295782 A 10/1992
JP 05-040100 A 2/1993
(Continued)

OTHER PUBLICATIONS

K. Marumoto, et al., "Electron Spin Resonance of Field-Induced Polarons in Regioregular Poly(3-alkylthiophene) Using Meta-Insulator-Semiconductor Diode Structures," J. Phys. Soc. Japan, vol. 74, No. 11, Nov. 2005, pp. 3066-3076, 2005 The Physical Society of Japan.
(Continued)

*Primary Examiner* — Melissa Koval
(74) *Attorney, Agent, or Firm* — Cermak Nakajima LLP; Tomoko Nakajima

(57) ABSTRACT

An electron spin measuring device of the organic thin film element is provided with: at least one sample tube into which a sample for measurement is inserted and which is sealed together with specific gas or with vacuum; a cavity into which the at least one sample tube is inserted; an electric characteristic measuring device for the characteristic evaluation of the organic thin film element which is the sample; connected wiring for interconnecting the electrical characteristic measuring device and the sample for measurement in the sample tube; and a light receiving/emitting device for performing the light irradiation to the sample for measurement, and/or performing the detection of the light emission from the organic thin film element, wherein the cavity resonator irradiates microwaves having the number of vibration corresponding to the Zeeman energy splitting of the unpaired electron, sweeps a magnetic field to the sample tube, and measures the transition between the energy levels caused by the reversal of the direction of the electron spin.

7 Claims, 21 Drawing Sheets

(56) References Cited

U.S. PATENT DOCUMENTS

| | | | |
|---|---|---|---|
| 6,259,203 B1 * | 7/2001 | Kawamura et al. | 313/506 |
| 6,602,714 B1 * | 8/2003 | Tagge et al. | 506/37 |
| 6,793,967 B1 * | 9/2004 | Ata et al. | 427/249.1 |
| 6,806,714 B2 * | 10/2004 | Izumi et al. | 324/318 |
| 6,815,067 B2 * | 11/2004 | Ata et al. | 428/408 |
| 7,704,923 B2 * | 4/2010 | Xiang et al. | 506/7 |
| 7,786,431 B1 * | 8/2010 | Donofrio et al. | 250/251 |
| 8,334,727 B2 * | 12/2012 | Gregg et al. | 331/96 |
| 8,614,438 B2 * | 12/2013 | Mitsui et al. | 257/40 |

FOREIGN PATENT DOCUMENTS

| | | |
|---|---|---|
| JP | 05-157712 A | 6/1993 |
| JP | 09-178727 A | 7/1997 |
| JP | 2001-174536 A | 6/2001 |
| JP | 2002-257759 A | 9/2002 |
| JP | 2004-264092 A | 9/2004 |
| JP | 2006-278583 A | 10/2006 |
| JP | 2007-048259 A | 2/2007 |
| JP | 2008-091467 A | 4/2008 |

OTHER PUBLICATIONS

K. Marumoto, et al., "Spatial Extent of Wave Functions of Gate-Induced Hole Carriers in Pentacene Field-Effect Devices as Investigated by Electron Spin Resonance," Phys. Rev. Lett. 0031-9007/06/97(25)/256603(4), 2006 The American Physical Society.

K. Marumoto, et al., "Electron Spin Resonance Observation of Gate-Induced Ambipolar Charge Carriers," Japanese J. Appl. Phys., vol. 46, No. 48, 2007, pp. L1191-L1193, 2007 The Japan Society of Applied Physics.

International Search Report for PCT Patent App. No. PCT/JP2009/005094 (Dec. 8, 2009).

* cited by examiner

ELECTRON SPIN MEASUREMENT DEVICE AND MEASUREMENT METHOD

This application is a national phase entry under 35 U.S.C. §371 of PCT Patent Application No. PCT/JP2009/005094, filed on Oct. 2, 2009, which claims priority under 35 U.S.C. §119 to Japanese Patent Application No. 2008-259622, filed Oct. 6, 2008, and Japanese Patent Application No. 2008-282823, filed Nov. 4, 2008, all of which are incorporated by reference.

TECHNICAL FIELD

The present invention relates to an electron spin measuring device and measuring method, more specifically relates to an electron spin measuring device which contributes to improve the performance of an organic thin film elements.

BACKGROUND ART

The research aimed at the applications of organic thin film elements in electronics is actively being carried out whereas the development research organic devices such as field-effect transistor (FET: Field Effect Transistor), organic electroluminescent elements (EL; Electro Luminescence, hereafter also referred to as organic EL elements), a solar battery and like is also being promoted as the organic thin film elements. The organic FET (Field Effect Transistor) has received widespread attention because the characteristic of the organic FET surpasses the characteristic of an amorphous silicon FET. The organic EL elements have received widespread attention and have put to practical use since they essentially comprise of characteristics of high intensity display for light emission surpassing those of liquid crystals.

The conventional method of evaluation of general organic thin film elements is carried out by the evaluation of the electrical conductivity property, or the evaluation of the crystal structure using by X rays. X ray diffraction which uses the phenomenon of X ray diffraction by the crystal lattice is a representative example of an evaluation method using X rays. The X ray is an electromagnetic wave with short wavelength wherein it is a technique which determines the alignment of the elements inside the crystal by analyzing the results of diffraction. However, when the X rays are applied on the macro size sample, the X rays penetrate only a few hundred mm of its surface. Therefore, the X ray diffraction method is an evaluation method restricted to the purpose of examining the crystal structure limited to the surface of its material. As described, the state and the electrical conduction mechanism of the electric charge carrier of the organic surface layer could not be ascertained by the conventionally used macro evaluation method.

In contrast, the evaluation method of micro phenomenon involves focusing on the unpaired electron which exists in the magnetic material, observing the spin state and directly evaluating the electrical conduction mechanism. The electron has a spin property, and since it consists of the angular momentum and the magnetic moment, if the magnetic field is added, the energy state of the spin of the unpaired electron is split into two levels. Using this phenomenon, a resonance phenomenon is observed in the sample comprising of an unpaired electron in the material, due to the absorption of microwaves in accordance with the transition of spin of the unpaired electron, in the magnetic field of a few thousand Gauss.

Therefore, the electron spin condition of the unpaired electron can be observed by trapping the several electric charge carriers after keeping the electric charge carrier in the material, in the stationary state. Owing to these reasons, the results of measurement in the organic field effect device which can use the insulating layer in which the electric charge carriers can be trapped are reported. For example, the molecular assembly structure in the device and the electron state of the electric charge carrier which has filled the electrical field in the structure have been determined by the microscopic evaluation using the observation of electron spin state in MIS (Metal Insulator Semiconductor) interface, TFT (Thin Film Transistor) or FET interface.

The inventors, by using a method which directly evaluates the electron spin, observed the state of the electric charge carrier accumulated in the MIS interface and FET interface as the organic thin film using the insulating layer, and evaluated the spatial extent of electrical charge having a deep correlation with the characteristics of the device and the molecular orientation of the organic molecule (refer to Non-Patent Literature 1~3 and the like).

On the other hand, it is difficult to understand the accumulation of electric charge carrier in the organic thin film solar battery which does not use the insulating layer, and besides, it is essential to further illuminate the light for the organic thin film solar battery wherein the electron spin in the organic thin film solar battery structure is not evaluated. The method of evaluation comprising the change in the quality of material due to the deterioration of the material for painting the automobiles is an example reported as an usage example of electron spin resonance phenomenon for the evaluation of an organic macromolecule compound or an organic material formed from an organic macromolecule which combines an organic compound and an inorganic compound (Refer to Patent document 1 and the like).

The cases which make use of the electron spin resonance phenomenon in the development of the organic EL elements, for the evaluation of the substrate of the organic EL are illustrated. Here, the substrate and the electrode layer formed on the substrate in the pattern shape are formed so as to cover the electrode layer, the photo catalyst containing layer is exposed to the ultraviolet rays and the electron spin resonance spectral is measured for the substrate for organic EL elements comprising a photo catalyst and a binder wherein the photo catalyst containing layer changes the wetting using the action of photo catalyst in accordance with the energy radiation (Refer to Patent document 2 and the like).

Further, the example is of an organic thin film solar battery which achieves high efficiency by focusing on the unpaired electrons. It is an organic thin film solar battery in which the hole retrieval layer comprises a low molecular compound containing a conductive macromolecular material and an unpaired electron, for the organic thin film solar battery comprising a first electrode later formed on the substrate, a hole retrieval layer, a photoelectric conversion layer and a second electrode layer. The focus is on the unpaired electron however the electron spin is not measured. The hole migration of the conductive polymer is smoothly carried out and the incident photon-to-current conversion efficiency is improved. (Refer to Patent Document 3 and the like)

Further, the cases have been proposed in which two sets of sample chamber formed from the sample and the cavity resonator are used for the time-resolved electron spin resonance phenomenon measurement method and the device (Refer to Patent Document 4 and the like).

There is another publication of application as for the organic thin film solar cell battery and the coating solution for forming the photoelectric conversion layer (see Patent document 5 and the like).

Non-Patent Document 1: K. Marumoto et al. "Electron Spin Resonance of Field Induced Polarons in Regioregular Poly (3-alkylthiophene) Using Metal Insulator Semiconductor Diode-Structures", Journal of the Physical Society of Japan 74(11) (2005) 3066-3076

Non-Patent Document 2: K. Marumoto et al. "Spatial Extent of Wave Functions of Gate Induced Hole Carriers in Pentacene Field Effect Devices as Investigated by Electron Spin Resonance", Physical Review Letters 97(25) (2006) 256603-1-256603-4

Non-Patent Document 3: K. Marumoto et al. "Electron Spin Resonance Observation of Gate Induced Ambipolar Charge Carriers in Organic Devices", Japanese Journal of Applied Physics 46(48) (2007) L1191-L1193

Patent document 1: Japanese Unexamined Patent Application Publication No. H9-038078

Patent document 2: Japanese Unexamined Patent Application Publication No. 2007-48529

Patent document 3: Japanese Unexamined Patent Application Publication No. 2006-278584

Patent document 4: Japanese Unexamined Patent Application Publication No. 2002-257759

Patent document 5: Japanese Unexamined Patent Application Publication No. 2008-91467

DISCLOSURE OF THE INVENTION

Problems to be Solved by the Invention

It is absolutely imperative that research and development is promoted with the understanding of the electric charge carrier state and the understanding of the essential conduction mechanism of the organic layer boundary surface for the performance improvement of the organic thin film elements. the micro evaluation should be carried out as an evaluation method by directly measuring the electric charge carrier accumulated on the organic layer boundary surface in the presence of actual conditions. For the purpose, the direct observation of the electric charge carrier after irradiation of the solar battery to the organic thin film solar battery is considered as effective, however, conventionally, there were no cases in which the micro evaluation of the organic thin film elements is carried out and the direct observation method was considered as necessary for the enhancement of the characteristics.

The present invention aims to provide a device and a method for measuring the spin resonance phenomenon of unpaired electrons to perform micro evaluation in the state observation of the electric charge carrier in an organic film interface while receiving light irradiation or the light emission from organic thin film elements and to provide an electron spin measurement device and the measurement method in order to improve the characteristics, for solving the problems described above.

Means for Solving the Problems

The inventors of the present invention accomplished the invention described below by focusing on the fact that the measurement of the electron spin which can observe the state of the electric charge carrier in the organic film interface during the driving and non-driving state of the organic thin film elements, is quite useful.

(1) An apparatus for measuring an electron spin of organic thin film elements, comprising: at least one sampling tube inserting samples into the apparatus and sealing the samples with a specified gaseous body or vacuum; and a cavity resonator into which at least one of the sampling tubes is inserted; the apparatus for measuring an electron spin of an organic thin film elements comprising: an apparatus for measuring electric characteristics for evaluating an organic thin film elements as a sample; wiring connecting the electrical characteristic measuring device to the samples in the sampling tube; and light receiving/emitting device irradiating light to the samples and/or detecting emission from the organic thin film elements; the cavity resonator irradiates a microwave supporting Zeeman energy splitting of unpaired electrons and sweeping a magnetic field in the sampling tube to measure a transition between energy levels produced upon reversing the direction of electron spin.

The electron spin measurement device described in (1) is equipped with at least one sampling tube inserting samples into the apparatus and sealing the samples with a specified gaseous body or vacuum; and a cavity resonator into which at least one of the sampling tubes is inserted; the apparatus for measuring an electron spin of an organic thin film elements comprising: an apparatus for measuring electric characteristics for evaluating an organic thin film elements as a sample; wiring connecting the electrical characteristic measuring device to the samples in the sampling tube; and light receiving/emitting device irradiating light to the samples and/or detecting emission from the organic thin film elements; the cavity resonator irradiates a microwave supporting Zeeman energy splitting of unpaired electrons and sweeping a magnetic field in the sampling tube to measure a transition between energy levels produced upon reversing the direction of electron spin. Therefore, it is possible to observe the electric carrier state in the driving and non-driving state of the organic film interface, the electron spin can be measured.

The electron has a property known as spin, and since it consists of the angular momentum and the magnetic moment, the energy state of the unpaired electron spin is split into two levels when the magnetic field is added. The spin at the lower level of energy is termed as $\alpha$ spin whereas the spin at the higher level of energy is termed as $\beta$ spin. The hourly average of the magnetic moment for $\alpha$ spin is parallel to the magnetic field whereas it is anti-parallel in case of $\beta$ spin. In case of paramagnet, the occupancy of two levels is determined by using Boltzmann distribution wherein 5 when the number of $\alpha$ spin and $\beta$ spin are compared, the number of $\alpha$ spin are marginally higher and the sum of entire magnetic moment becomes parallel to the magnetic field. When the unpaired electrons are kept in a stationary magnetic field, the parallel and the antiparallel states are formed in the magnetic field resulting in the difference in two types of magnetic energies produced by the unpaired electrons. The electron spin can be measured by irradiating the electromagnetic waves of the microwaves spectrum corresponding to these two energy differences and observing the absorption of magnetic waves. Particularly, since the organic thin film solar battery is operated by light irradiation, this measurement is carried out without the light irradiation from the solar stimulator acting as an emitting device in the non-driving state, and further, in the driving state, the measurement is carried out by irradiating the light from the solar stimulator in the measured objects through the optical penetration window of the cavity resonator. The unpaired electrons either do not exist or exist in a very small amount by making the substrate and the electrode non-magnetic or feebly magnetic, wherein only the unpaired electrons accumulated on the organic film layer can be measured.

(2) The electron spin measuring device of the organic thin film elements described in (1), further comprising: a control apparatus which connects the electrical characteristics measuring device and the light receiving and emitting device by a communication line, wherein the electron spin measuring device measures the characteristic of the organic thin film elements and the characteristic of the electron spin at the same time and outputs temporal change data of the both characteristics.

According to the invention described in (2), for the organic thin film elements of the measuring objects, since the relay terminal is connected with the electrode, the electron spin can be measured by measuring the current-voltage characteristics of the organic thin film elements and monitoring the electrical state. Therefore, particularly, the relation of the electrical characteristics with the electron spin becomes clear. Further, since it is equipped with an emitter which carries out light irradiation from the organic thin film elements and/or emission detection from the organic thin film elements, and the electrical characteristics measurement device and the emitter are mutually connected to the control device through the telecommunication line, so the organic thin film elements.

(3) The electron spin measuring device of the organic thin film elements described in (1) or (2), wherein the cavity resonator comprises an optical penetration window substantially having no negative effect to wavelength dispersion of refraction index in wavelength ranges from visual light to far-red light because of illuminating light to the samples and/or detecting emission from the samples available.

The electron spin measurement device described in (3) is equipped with an optical penetration window substantially having no negative effect to wavelength dispersion of the refraction index ranging from visual light to far-red light because of irradiating light to the samples and/or detecting emission from the samples. Therefore, the emitter can receive the light which emits from the organic thin film elements through the optical penetration window, and further, the light from the emitter can be irradiated in the organic thin film elements acting as a sample.

(4) The electron spin measuring device of the organic thin film elements described in (1) or (2), wherein the cavity resonator and the at least one sampling tube are respectively equipped with a means independently rotatable in a concentric fashion for the sample in the at least one sampling tube as a point target for arbitrarily varying magnetic direction and/or light illuminating direction available against a surface of the sample positioned in the at least one sampling tube.

According to the description in (4), since the cavity resonator and the sampling tube are respectively equipped with a means independently rotatable in a concentric fashion for the sample in the sampling tube as a point target because of arbitrarily varying magnetic direction and/or light illumination direction available against a surface of the sample positioned in the sampling tube, and since the measurement can be done by changing the angle in the sample, the factors to determine the characteristics can be easily clarified.

(5) The electron spin measuring device of the organic thin film elements described in (1) or (2), wherein the cavity resonator comprises a rotation band rotatable with the light receiving and emitting device provided on an outer circumference of the cavity resonator, and wherein the rotation band and the sampling tube respectively and independently rotates concentrically and symmetrically about a point of the sample in the sampling tube.

According to the invention described in (5), the cavity resonator comprises a light receiving/emitting device provided on the outer circumference of the cavity resonator, and a rotatable rotation band, wherein the rotation band is respectively and independently rotatable together with the sampling tube in a concentric fashion for the sample in the sampling tube as a point target. Therefore, the sample in the sampling tube can be tested by independently rotating the emitter.

(6) The electron spin measuring device of the organic thin film elements described in (5), wherein the rotation band is composed of nonmagnetic materials and equipped with a gear rotation mechanism.

According to the invention described in (6), since the rotation band is composed of a non-magnetic material and equipped with a gear rotation mechanism in an electron spin device of the organic thin film elements as per the present invention described in (4), the rotation band can be accurately adjusted and measured at the desired position.

(7) The electron spin measuring device of the organic thin film elements described in any one of (1) to (7), further comprising a means of transferring sample tubes for adjusting the magnetic direction, light illuminating direction against a surface of a sample positioned in the sampling tube, and/or direction of light emission from the sample.

The electron spin measurement device described in (7) is equipped with a means of transferring sample tubes for adjusting a magnetic direction, light illuminating direction against a surface of a sample positioned in the sampling tube, and/or direction of light emission from the sample. Therefore, accurate data can be obtained by adjusting the measurement sensitivity of the sample to a higher position.

(8) The electron spin measuring device of the organic thin film elements described in any one of (1) to (7), wherein the light receiving and emitting device uses an optical fiber or a light guiding body.

The electron spin measuring device of an organic thin film elements described in (8) is a photo and luminescent detector using an optical fiber or a light guiding body. Therefore, the sampling tube can be easily moved for the measurement and it can also be used even when 5 it is rotating.

(9) The electron spin measuring device of the organic thin film elements described in (6) or (7), further comprising: extracting functional part electron spin resonance signal means for extracting only electron spin resonance signal in a specified functional part in comparison with a plurality of electron spin resonance signals of the samples.

The electron spin measuring device of an organic thin film elements described in (9) is further equipped with a means of extracting a functional partial electron spin resonance signal by only extracting electron spin resonance signal in a specified functional part in comparison with a plurality of electron spin resonance signals of the samples. Therefore, since only the electron spin resonance signal of a specified functional part is extracted after comparing the electron spin resonance signals of multiple samples, the measured data can be easily analyzed.

(10) The apparatus for measuring an electron spin of an organic thin film elements described in any one of (1) to (9), wherein a wavelength of the microwave is 3 cm (X band in frequency of 10 GHz band) long, the strength of the microwave is not lower than 0.01 mW and not higher than 2 mW, and the modulated magnetic field is not lower than 0.001 tesla and not higher than 0.1 tesla.

The wavelength of the microwaves is 3 cm (frequency is X band of 10 GHz band), the strength of the microwaves is from 0.01 mW or more to 2 mW or less, and the magnetic field modulation is from 0.001 Tesla or more to 0.1 Tesla or less, for the electron spin measuring device of an organic thin film elements described in (10). When the microwave output is 0.01 mW or less, it covers the ESR signal strength at the noise level. Further, when the microwave output exceeds 2 mW, the correct ESR signal is not obtained due to the saturation phenomenon. Therefore, it is easy to analyze the measured data which has an appropriate range for research and development of the organic thin film elements.

(11) The electron spin measuring device of the organic thin film elements described in (8), further comprising: accumulated electron charge carrier information calculating means for calculating a site producing an electric charge carrier, an electric charge type, and a concentration of stored electric carrier, from g value of spectral branching factor, a line width ΔH, and a line shape of the electron spin resonance signal which are obtained from an electron spin resonance signal.

The electron spin measuring device of an organic thin film elements described in (11) is further equipped with a means of calculating stored electric charge carrier information: the site at which the electric charge carrier was produced, the electric charge type, and the concentration of stored electric charge carrier, from value g, the spectrum branching factor obtained from an electron spin resonance signal, ΔH, the line width, and the line shape of the electron spin resonance signal. The site at which the electric charge carrier was produced, the electric carrier type, and the concentration of the stored electric charge carrier are calculated by using the means of calculating the stored electric charge carrier information. Therefore, since the state of the electric carrier state can be tracked, it contributes to attaining appropriate solutions.

(12) A method of measuring electron spin of an organic thin film elements comprising: providing separately on a substrate or a plurality of substrates a first sample composed of organic thin film elements, a second sample excluding organic functional thin films from the organic thin film elements, and at least two samples including the first and second samples; inserting the separated samples into a sampling tube; sealing the sampling tube with a specified gas or in vacuum; inserting the sampling tube into a cavity resonator; irradiating a microwave having a vibration frequency corresponding to Zeeman energy splitting produced by unpaired electrons, to each of a first sample and a second sample displacing a position while sweeping a magnetic field, and at the same time, measuring a transition between energy levels produced upon reversing the direction of electron spin; executing a differential treatment of a first electron spin resonance signal from the first sample composed of organic thin elements, a second electron spin resonance signal from the second sample excluding the organic functional thin films from the organic thin film elements, and a third electron spin resonance signal from a sample excluding partially the organic functional thin films from the organic thin film elements; and extracting only components of the electron spin resonance signals derived from the organic functional thin films.

The method of measuring the electron spin of an organic thin film elements described in (12), is comprised of using a first sample composed of organic thin film elements, a second sample excluding organic functional thin films from the organic thin film elements, and at least two samples including these samples, pasting these samples on the same substrate, or on another substrate to obtain separated samples, inserting the separated samples in a sampling tube, sealing the sampling tube with a specified gas, or in vacuum, inserting the sampling tube into a cavity resonator, irradiating a microwave having frequency supporting Zeeman energy splitting of unpaired electrons to each of a first sample and a second sample displacing a position while sweeping a magnetic field, and at the same time, measuring the transition between energy levels produced upon reversing the direction of electron spin, executing a differential treatment of an electron spin resonance signal from the first sample composed of organic thin elements, an electron spin resonance signal excluding the organic functional thin films from the organic thin film elements, an electron spin resonance signal from the sample excluding a part of the organic functional thin films from the organic thin film elements and extracting only components of the electron spin resonance signals derived from the organic functional thin films. Therefore, the data can be easily analyzed by appropriately creating the first sample and the second sample.

(13) The electron spin measuring method of the organic thin film elements described in (12), wherein the organic thin film elements is an organic thin film solar battery punching at least either one of a P type organic semiconductor or an N type organic semiconductor forming a boundary surface in contact with each other between a positive pole and a negative pole, the cavity resonator comprises an optical penetration window for illuminating artificial sunlight produced by a solar simulator, or a dispersed light produced by a spectral instrument, and increased sites of unpaired electrons produced by driving the organic thin film solar battery, or modified sites in organic layers identified from a change of the signal shape of the electron spin resonance signal in the organic thin film layers before and after driving upon illuminating light.

According to the electron spin measuring method of the organic thin film elements described in (13), an optical penetration window for illuminating artificial sunlight produced by a solar simulator, or a dispersed light produced by a spectral instrument, and increased sites of unpaired electrons produced by driving the organic thin film solar battery, or modified sites in organic layers are specified from a change of a signal shape of an electron spin resonance signal in the organic thin film layers before and after activating light illumination. Therefore, since the organic thin film solar battery can examine the state of the electron spin before and after driving, it proves useful for the research and development of the organic thin film solar battery.

(14) The electron spin measuring method of the organic thin film electroluminescence elements described in (12), wherein the organic thin film elements are organic electroluminescence elements at least punching organic emission layers in contact with each other between a hole injection electrode and an electron injection electrode, the cavity resonator comprises an optical penetration window for measuring light emitted from the organic electroluminescence elements, and increased sites of unpaired electrons produced by driving the organic electroluminescence elements, or modified sites in organic layers identified from a change of the signal shape of the electron spin resonance signal in the organic thin film layers before and after driving upon light emission.

According to the electron spin measuring method of the organic thin film elements described in (14), the optical penetration window for measuring the light emitted from the organic electro luminescence elements, and increased sites of unpaired electrons produced by driving the organic electro luminescence elements, or modified sites in organic layers are identified from a change of the signal shape of the electron spin resonance signal in the organic thin film layers before and after driving upon light emission. Therefore, the sampling tube can be easily moved for the measurement and can be used even when it is rotating. Therefore, since the organic thin film electroluminescent elements can examine the state of electron spin before and after driving, it proves useful for the research and development of the organic thin film electroluminescence elements.

Effect of the Invention

According to the present invention, the electron spin measuring device and the electron spin measuring method effective for the development of the organic thin film elements with improved performance, can be provided in which the simulated solar light is irradiated, further, the luminescence of elements is measured, and the micro evaluation can be carried out by the spin measurement of unpaired electrons of an organic thin film elements, and deterioration mechanism of an organic thin film elements can be clarified from the storage conditions of the electrical charge and guidelines for performance improvement of the organic thin film elements can be created based on the clarification.

Figure 1:
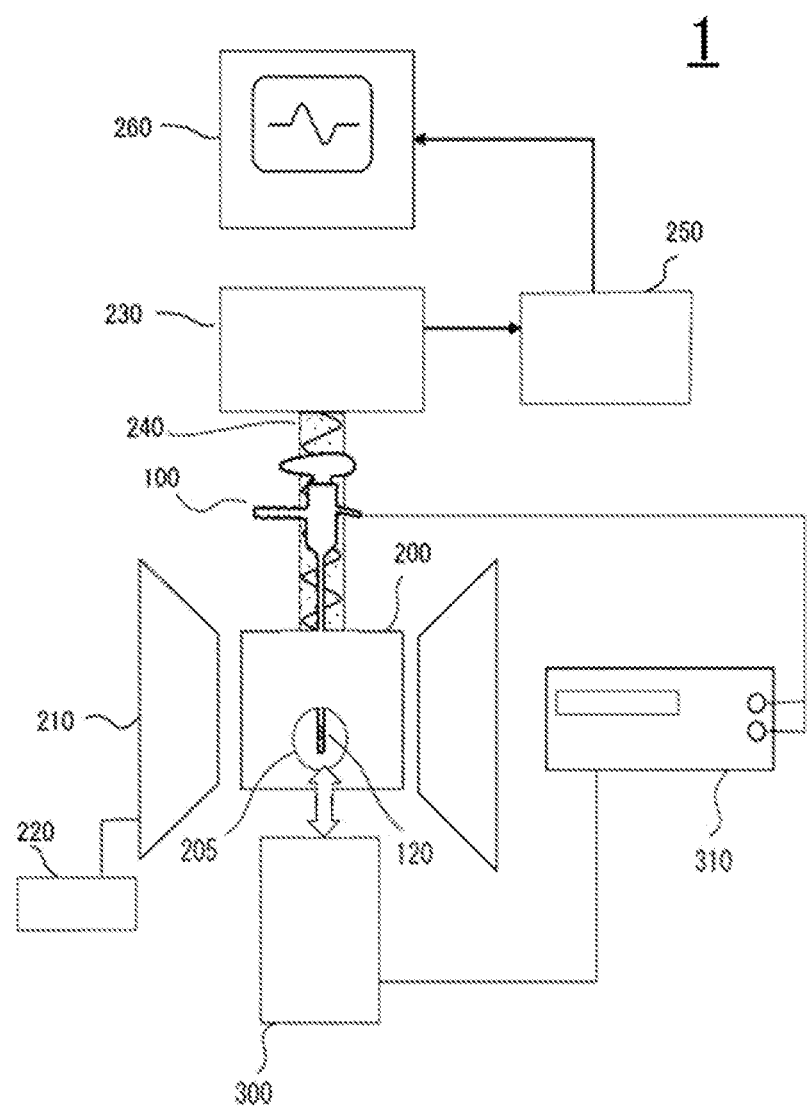
FIG. 1 is a block diagram of a preferred mode for carrying out this invention.

EXPLANATION OF SIGN 50 substrate
52 organic layer
54, 56 negative electrode
58 positive electrode
60, 62 wiring
100 sampling tube
120 sample for measurement
130 connection wiring
140 connection terminal 25
200 cavity resonator
205 penetration window
210 electromagnet
230 microwave bridge
240 circulator
250 phase sensitive detector
260 signal analyzer
300 light receiving/emitting device
310 electrical characteristics measuring device
400 control device
420 means for calculating the accumulated electron charge carrier information
440 means for extracting functional part electron spin resonance signal
500 rotation band

BEST MODE FOR CARRYING OUT THE INVENTION

Below, the embodiments of the present invention will be described. 5 Note that, these are only examples, and the technical range of the present invention is not limited hereto.

Embodiments

FIG. 1 is a schematic drawing of the electron spin measuring device 1. As shown in FIG. 1, a cavity resonator 200, an electromagnet 210, an excitation power supply 220, a microwave bridge 230, a circulator 240, a phase sensitive detector 250 and a signal analyzer 260 are attached to an optical penetration window 205 which does not have any negative effect to wavelength dispersion of refraction index, in the wavelength ranging from a visual light to a far-red light because of illuminating light to the samples and/or detecting the emission from the samples available. Then, there is a light receiving/emitting device 300 which irradiates light to the organic thin film elements and/or detects the emission from the organic thin film elements. In case of the organic solar battery, the simulated solar light from the light receiving/ emitting device 300 is irradiated and then measured by using the electrical characteristics measuring device 310 for the electrical evaluation of the elements. Further, the life characteristics after continuous light irradiation can also be measured by controlling the electrical characteristics device 310.

Figure 2:
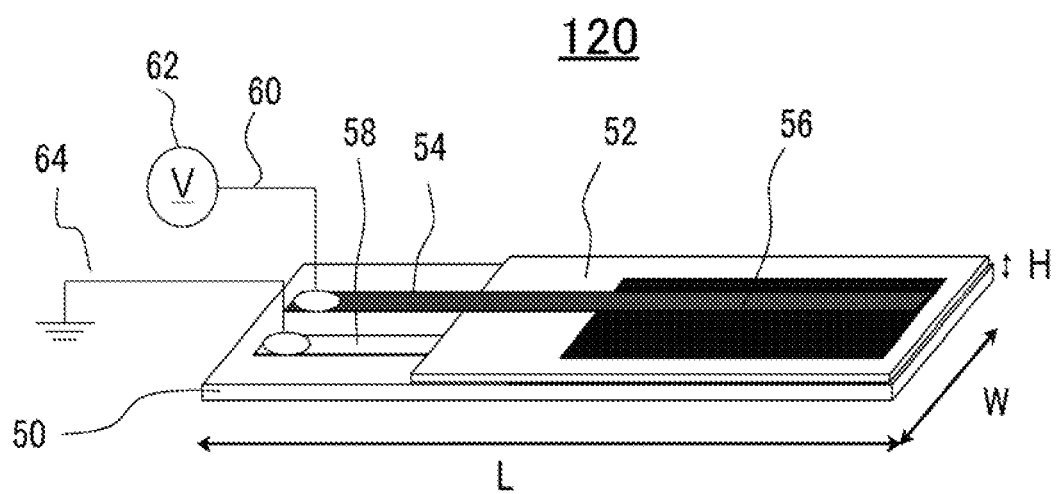
FIG. 2 is a measurement sample for carrying out this invention.

FIG. 2 shows the element structure manufactured for the measurement of the organic thin film elements used in the present invention. The organic layer 52 is wedged between a negative electrode 54 and a positive electrode 58 on a substrate 50 wherein it increases the area of electrode 56 of the electric charge carrier generated part. The organic thin film elements used for the measurement is connected to an external power supply 62 from negative electrode 54 by wiring 60 and grounded on the other side from positive electrode 58 by wiring 64 to enable external driving. It is necessary to use a non-magnetic or a feeble magnetic material for the electrode so that the presence of the unpaired electrons does not affect the measurement of the organic thin film elements. The area of elements activity should be increased and the number of unpaired electrons should be increased in order to raise the detection sensitivity. For this reason it is effective if the elements used for the measurement is a size that can be inserted in the sampling tube which can be measured by increasing the generation of electric charge carriers. Length L, width W and height H for the organic thin film elements used in the actual measurement are approximately 30 mm, 3 mm and 1 mm or less respectively.

Figure 3:
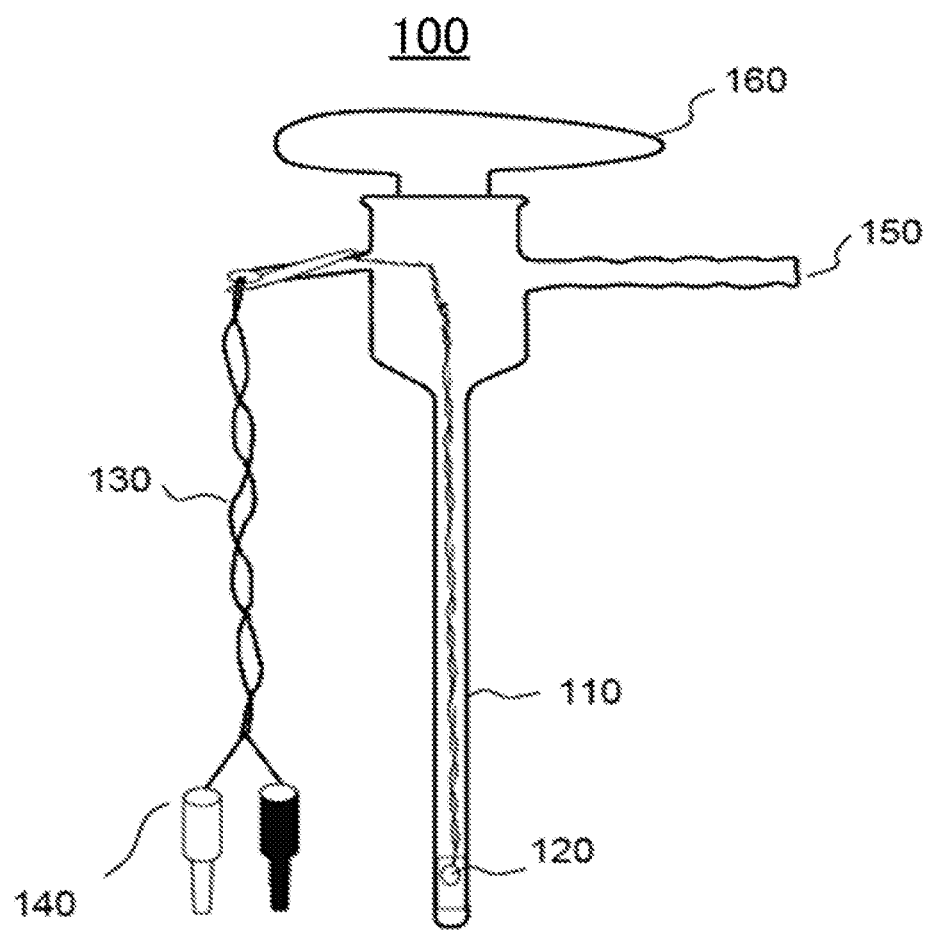
FIG. 3 is a measurement sample in the tube for carrying out this invention.

FIG. 3 is a state in which an element 120 manufactured for the measurement is set in a sampling tube 100 of electron spin measuring device 1. The element for the measurement 120 is positioned at the end of a narrow tube 110 of the sampling tube 100, the wiring 130 for the driving is pulled in the outer part of the sampling tube and a plug 140 to be inserted in the external power supply terminal is connected. A cork 160 which seals the sample insertion slot and an insertion opening 150 which makes the measurement environment a void and inserts each type of gaseous body, are installed in the sampling tube 100.

For the spin measurement of the unpaired electrons, a strong magnetic field is generated in the element used for the measurement 120 in the sampling tube 100 inserted in the cavity resonator 200 from the electromagnet 210 which has been excited by using the excitation power supply 220, the microwaves corresponding to the energy field known as Zeeman splitting which is made by the unpaired electrons (spin) illuminated by the microwave bridge 230 and the signal observed by the signal analyzer 260 is analyzed by detecting the absorption of the magnetic wave by the phase sensitive detector 250. The organic thin film element 120 can be measured even in the driving state by using the electrical characteristics measuring device 310. Usually, the resonance phenomenon is generated when the quantum energy of microwaves and the Zeeman energy generated by the unpaired electron are matched with each other.

The fundamental measurement procedure is described below; however, initially the preparation for the electron spin measurement device is described.

(1) For the manufacturing of organic thin film elements for the organic EL element or the organic solar battery and the like for which the electron spin measurement can be carried out, a sampling tube of quartz glass sample tube and the like which can be inserted in the cavity resonator of the measuring device, is used, and the organic thin film element 120 which can be inserted in the sampling tube is manufactured.

(2) After the completion of wiring for the manufactured element and the sampling tube, the organic thin film element 120 is inserted in the sampling tube and then it is encapsulated. The wiring is connected to the electrical characteristics measuring device 310 and the like of source meter and the like. Keeping the element in a drive available state, the electron spin measurement is carried out in the driving and non-driving state.

The electrical charge driving can be made as static as possible for a MIS boundary surface, TFT boundary surface and FET boundary surface, however, since the electrical charge carrier is operated during the driving of organic EL element without an insulating layer, the size of the magnetic field modulation should be reduced in order to observe the narrow signal form of the resonance phenomenon correctly since the line width of the resonance signal becomes narrow due to effect of the driving.

(3) The surroundings of the organic thin film element such as vacuum, inactive gases, oxygen, air and the like can change on their own by encapsulation of the organic thin film element. Accordingly, the effect of the surroundings of the element for the organic thin film element driving state, for example, the effect of oxidization and the like can also be clarified by using the electron spin measurement.

(4) The transparent plastic substrate and the like such as PET (Polyethylene Terephthalate) film and the like can also be used as a substrate as required as shown in FIG. 2.

(5) The ITO transparent electrode (Indium Tin Oxide) and the other electrodes of non-magnetic material such as zinc oxide and the like can also be used as the positive electrode as required as shown in FIG. 2.

(6) In addition to the metals, the conductive organic material such as PEDOT (Poly(3,4-Ethylene Dioxy Thiophene)) system and the like which does not consist of unpaired electrons and the other non-magnetic material showing conductive property such as the charge transfer complex and the like which is a molecule based material formed from a donor molecule and an acceptor molecule, can be used for the negative electrode as shown in FIG. 2.

(7) Other sizes can also be used, as required, for the size of the substrate shown in FIG. 2. There may be a case in which the presence of the unpaired electrons is hidden by the noise. If necessary, the measurement is carried out for the size in which the resonance phenomenon can be observed.

(8) Another sampling tube can also be used and then compared with the sampling tube attached with a cork shown in FIG. 3.

(9) The organic thin film part shown in FIG. 2 manufactures the organic thin film showing the functionality corresponding to the purpose of measurement.

Next, the actual measurement method is described.

Figure 4:
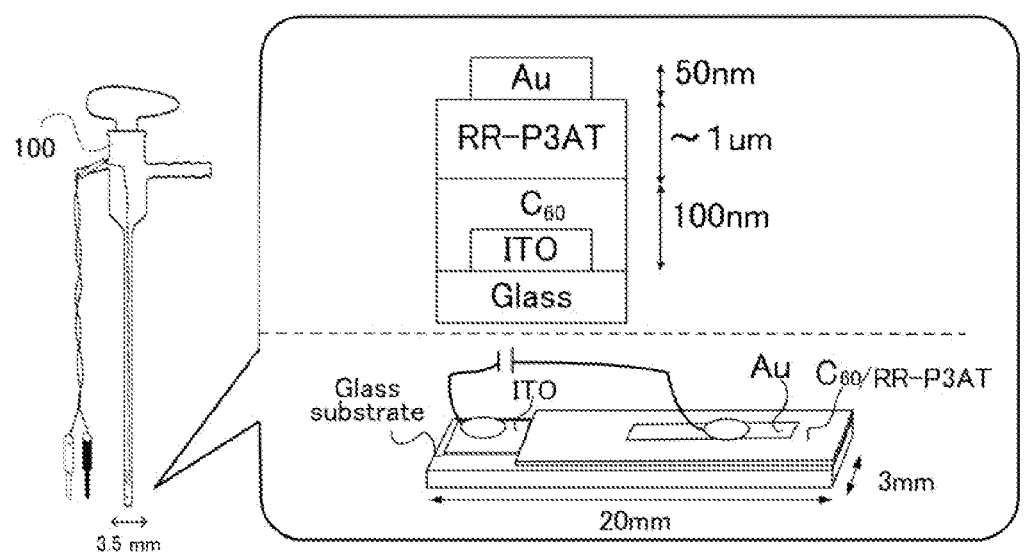
FIG. 4 is an example of a measurement sample in the tube for carrying out this invention.

(1) As shown in FIG. 4, the element for the spin measurement of hetero junction type high molecular organic thin film solar battery is inserted in the sampling tube 100 of the electron spin measuring device 1 of the present invention, then inserted in the cavity resonator (cavity) 200, and then is connected with the electrical characteristics measuring device 310 such as the source meter and the like.

(2) Various devices in the market such as JES-TE200X-band ESR spectrometer made by JEOL, EMX-X band ESR spectrometer made by Bruker, and the like can be used as the magnetic field generating units of the electron spin measuring device 1 of the present invention.

(3) TE011 cylindrical type cavity made by JEOL and the like can also be used as the cavity resonator 200.

(4) 261 2 type source meter unit, and 2400 type source meter unit made by KEITHLEY and the like can be used as the electrical characteristics measuring device 310.

(5) The electron spin resonance signals are measured. The microwaves entering into the microwave bridge are detected by the phase sensitive detector, the data is incorporated in the signal analyzer and the measurement results are analyzed. Further, for removing the effect of noise, the signals are integrated over a period of time and SN ratio is improved.

Figure 5:
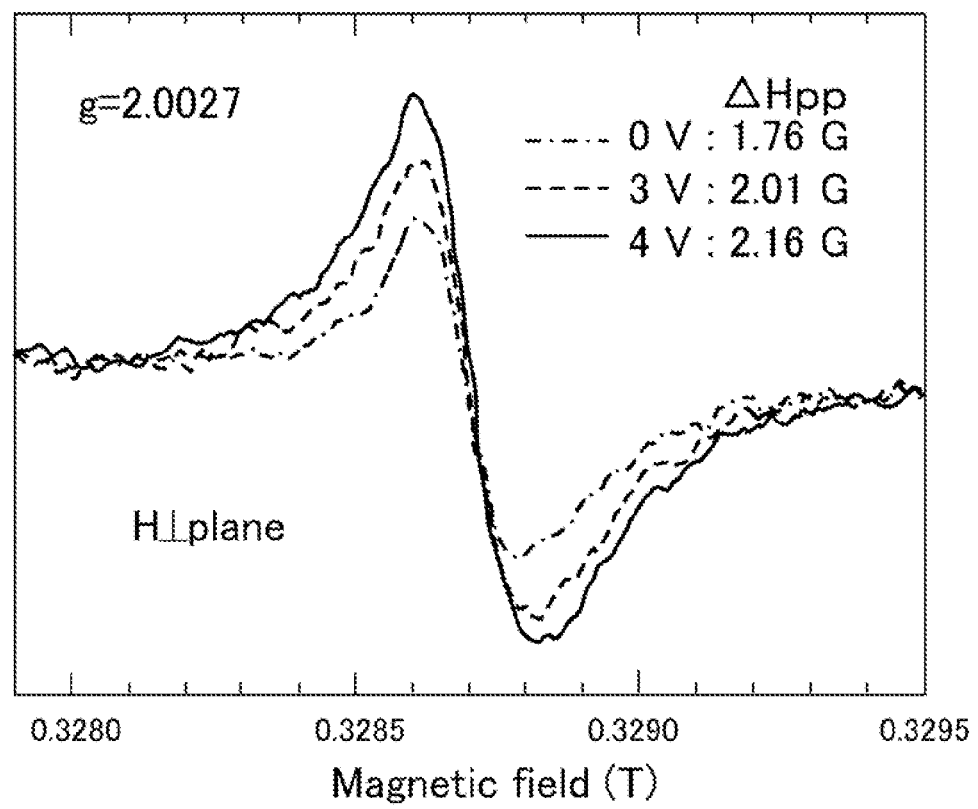
FIG. 5 is the measurement ESR signal data by the spin electron spin measurement device of this invention when the voltage on the sample device is changed.

FIG. 5 shows the measurement results obtained by changing the applied voltage. According to FIG. 5, the movement becomes difficult since the carriers are captured in the trap site after applying the voltage and encapsulating the carrier. Therefore, if the line width is to be increased, it can be done.

Figure 6:
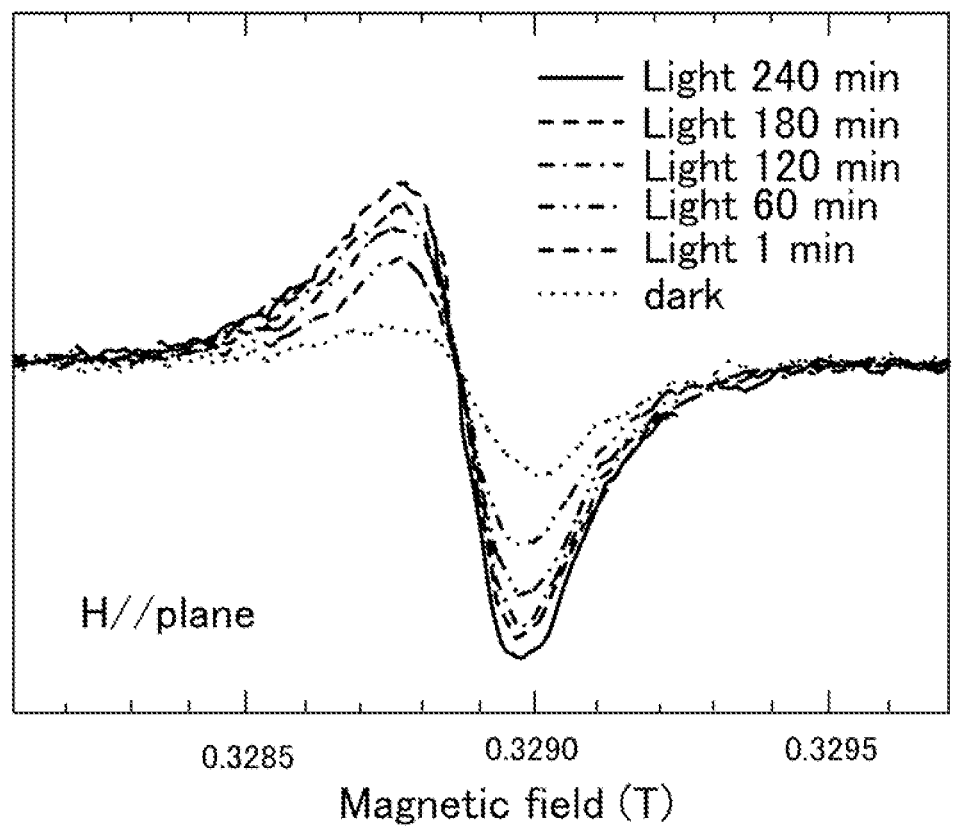
FIG. 6 is the measurement ESR signal data by the spin electron spin measurement device of this invention when the light irradiating time on the sample device is changed.

FIG. 6 is a diagram which shows the measurement of the change of irradiation time for the sample. It is clear that the signal is increased due to light irradiation and the positive polarity comprising of ½ spin by the generated carrier is detected. It was determined that the increase in the signal strength along with the time is related to the improvement in the photo electric current value (Jsc) of the laminated polymer solar battery element along with light irradiation time.

In this manner, the fundamental examination of the conduction mechanism can be carried out by measuring the resonance signal, however, the representative value of g is assumed. The value of g reflects the state of the electron orbit in which the electron is inserted. The magnetic ions and the defects, if any, in the elements can be identified by examining the value of g. The absorption strength of microwaves for the magnetic field H is recorded keeping the microwave frequency γ constant, the value H of magnetic field (resonant magnetic field) caused by absorption is measured and the value of g is calculated using the relation between Planck's constant h and Bohr magnetron β, in other words the relation formula of $g=h\gamma/\beta H$.

Then, since the value of g creating the resonant magnetic field of the signal is characterized by a material such as an organic material and the like, the points wherein the part of the element electrical charge is accumulated or which organic thin film element is changed, can be identified, and the characteristics of the organic thin film element can be clarified.

Embodiment 2

Figure 7:
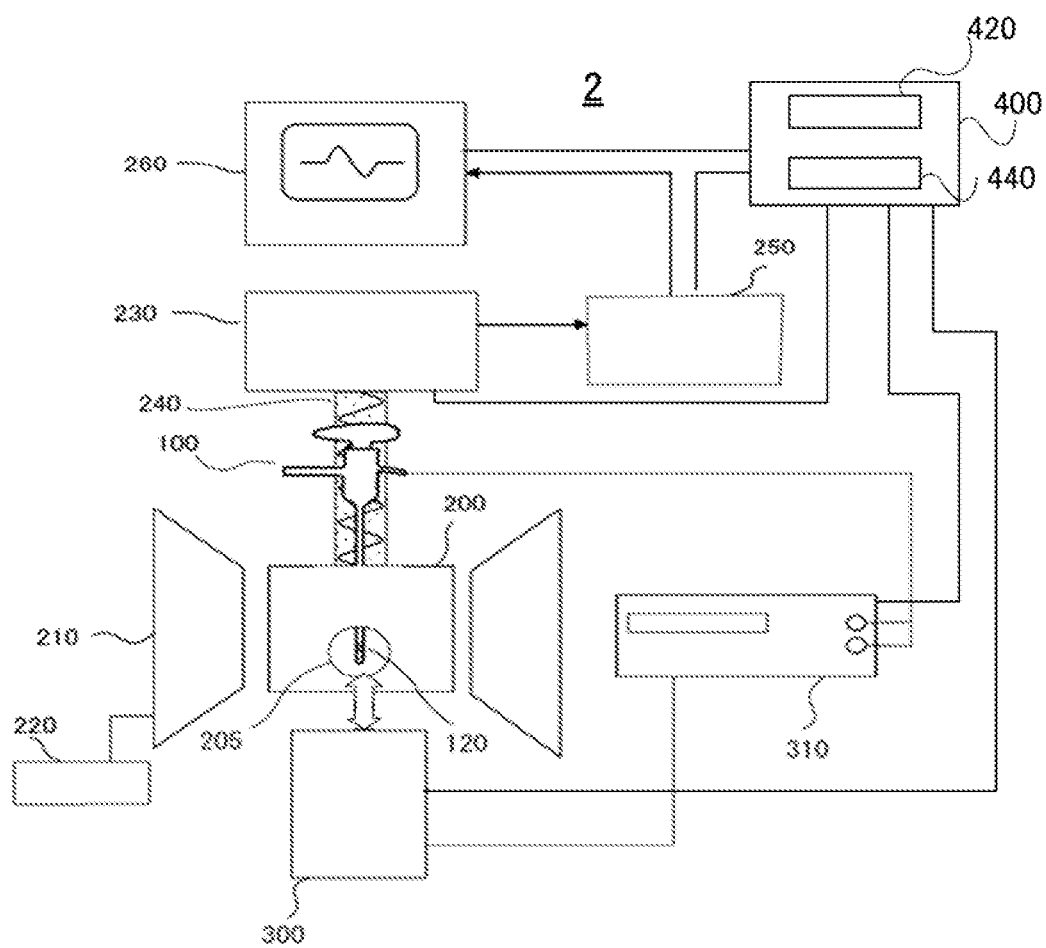
FIG. 7 is a block diagram of another preferred mode for carrying out this invention.

FIG. 7 is a schematic drawing of an electron spin measuring device which is another example of the present invention. As shown in FIG. 7, for the electron spin measuring device 2, the electron spin measuring device 1 consists of an external power supply 310 for driving the organic thin film element, a control device 400 which is connected mutually with the light receiving/emitting device 300 by the telecommunication line, a means for calculating the accumulated electron charge carrier information 420 in the control device 400 which calculates the generated region of electron charge carrier, electron carrier type, accumulated electron charge carrier concentration from the special branching factor g value, line width ΔH and line shape of electron spin resonance signal obtained from the electron spin resonance signal and a means for extracting functional part electron spin resonance signal 440 which extracts only the electron spin resonance signal of specified functional part by comparing electron spin resonance signals of several samples.

Figure 8:
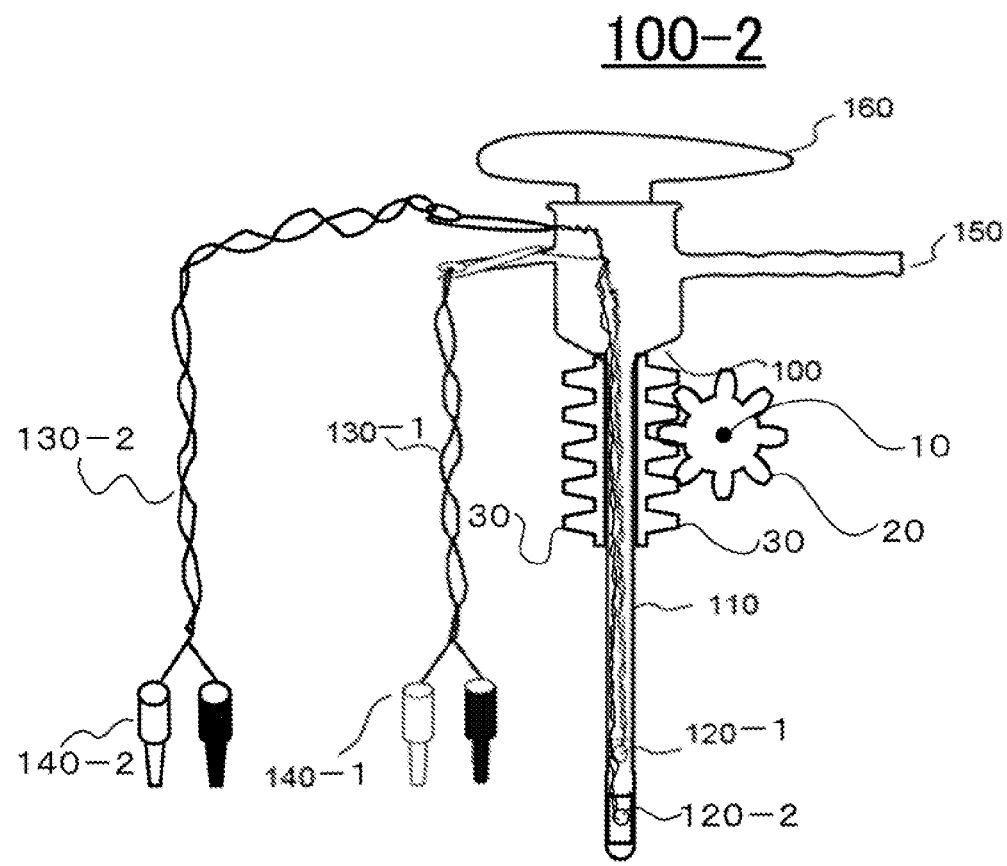
FIG. 8 is a measurement sample in the tube that is axially transferable for another preferred mode carrying out this invention.

Further, as shown in FIG. 8, the sampling tube 100-2 is equipped with a means for moving the sampling tube (from 10 to 30) for adjusting the magnetic field direction, irradiation direction and/or for adjusting the emission direction from the samples, for the surface of the sample positioned inside the sampling tube. Further, two types of samples such as sample 120-1 and sample 120-2 are inserted in the same sampling tube 100-2 and can be measured in the same condition by moving them using the means for moving the sampling tube. Further, since the wiring is individually set for 2 types of samples, the power supply can be changed independently for each sample and the output can be measured independently.

Figure 9:
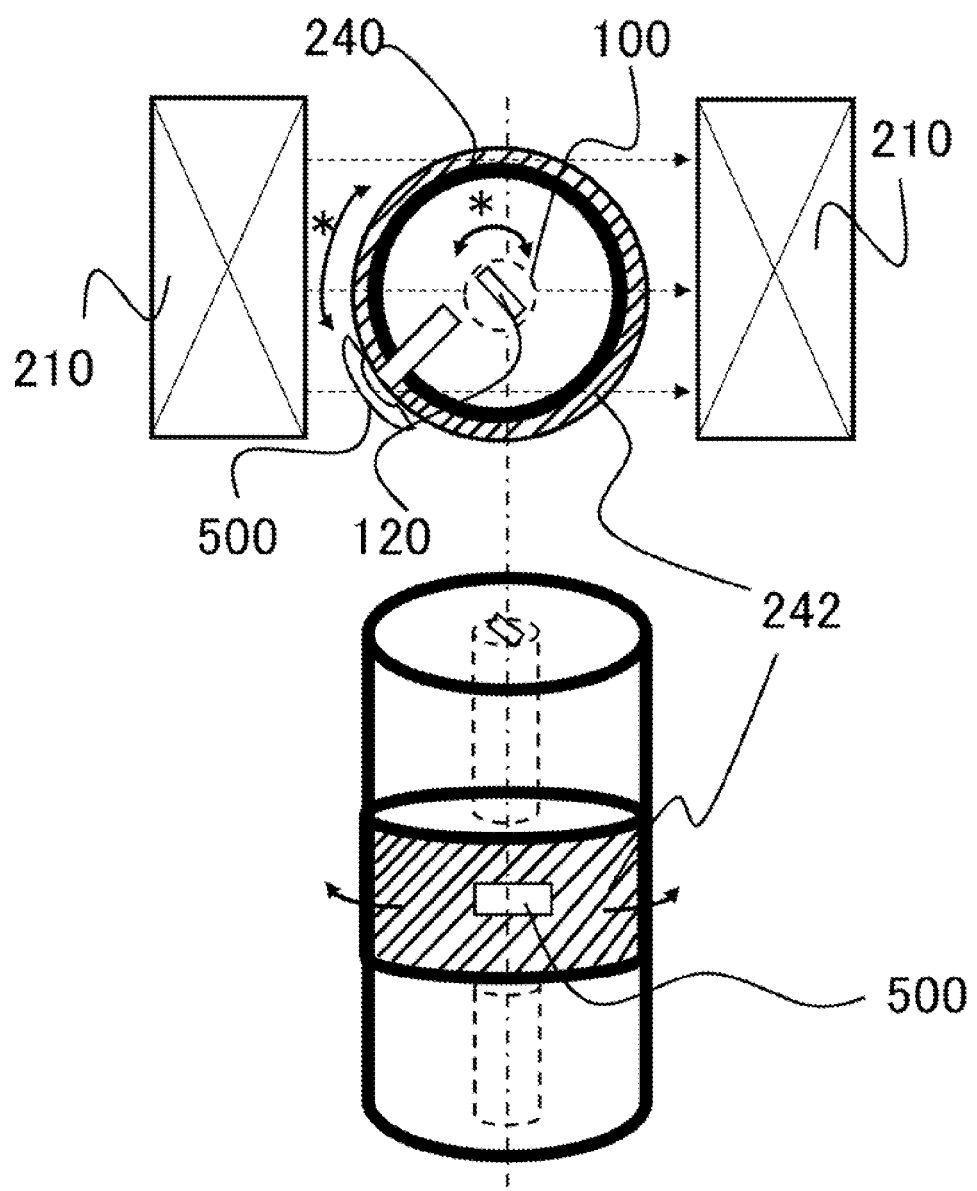
FIG. 9 is the tube that magnetic field or light irradiation to the sample is rotatable for another preferred mode carrying out this invention.
Figure 10:
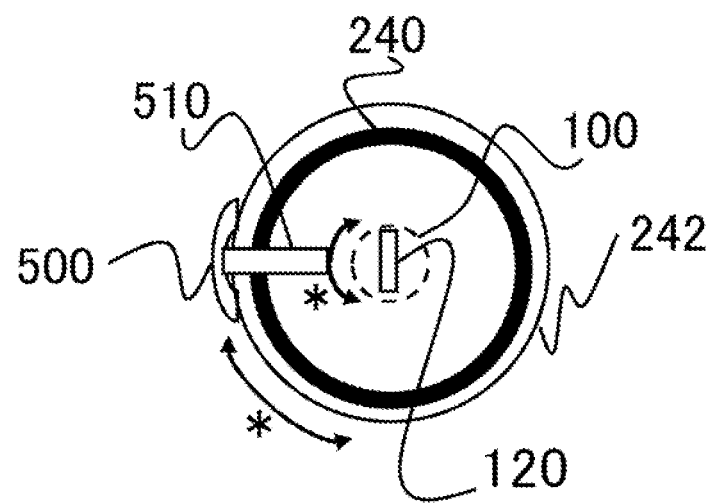
FIG. 10 is the tube that the magnetic field is perpendicular to the sample for another preferred mode carrying out this invention.
Figure 11:
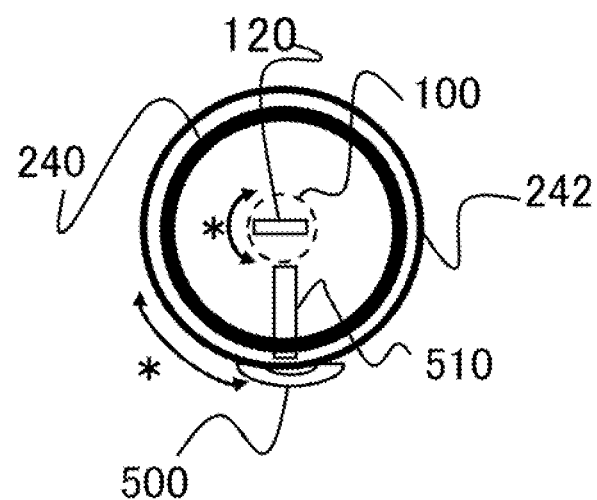
FIG. 11 is the tube that the magnetic field is parallel to the sample for another preferred mode carrying out this invention.

Further, as shown in FIG. 9 to FIG. 11, the cavity resonator 200 and the sampling tube 100-2 is equipped with a means which enables the independent rotation in the respective concentric fashion considering the sample inside the sampling tube as a point target for the surface of sample 120 positioned inside the sampling tube in order to arbitrarily adjust the magnetic direction and/or irradiation direction.

Also, the cavity resonator 200 comprises a rotation band 500 rotatable with a light receiving/emitting device 300 provided on the outer circumference of the cavity resonator, wherein the rotation band is respectively and independently rotatable together with the sampling tube 100 in a concentric fashion for the sample 120 in the sampling tube as a point target. The rotation band 500 is formed from a non-magnetic material and since it consists of a gear rotation mechanism, it can be rotated with precision.

Figure 13:
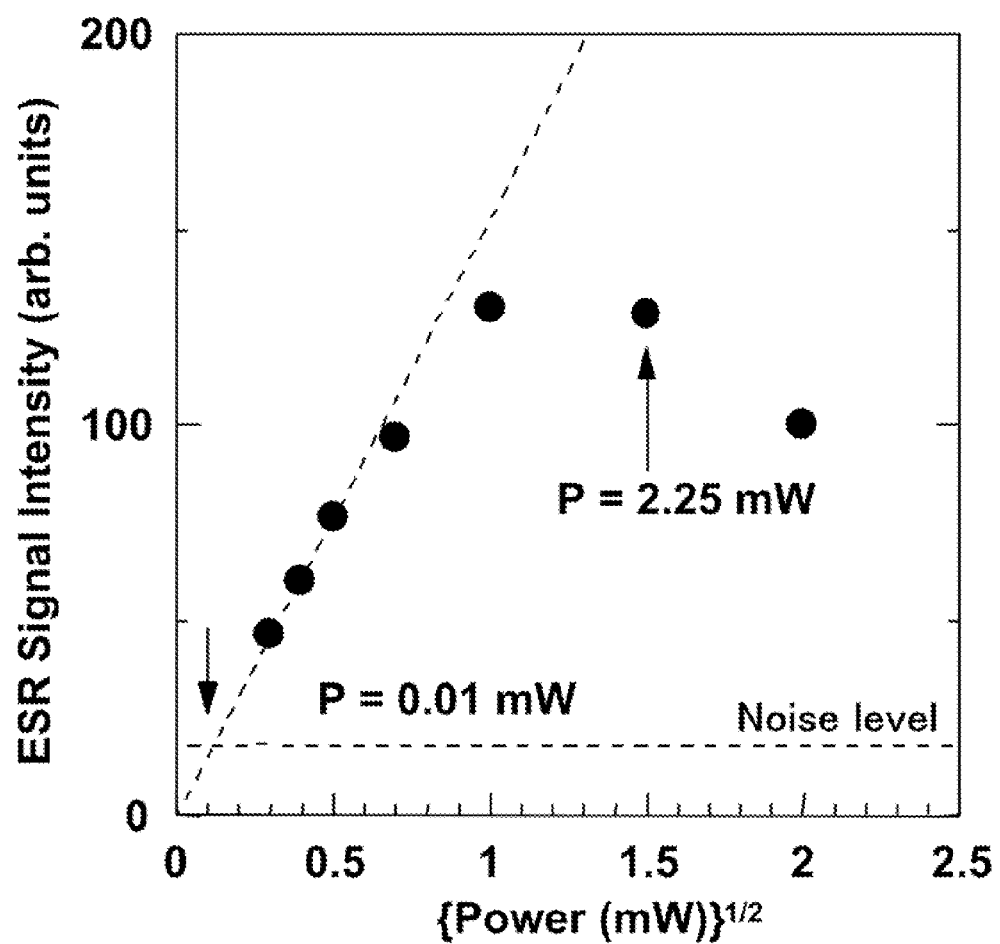
FIG. 13 is the data about ESR Signal intensity when micro wave power is increased.

The wavelength of microwaves is set to 3 cm (frequency is X band of 10 GHz band), the strength of microwaves is set to 0.01 mW or more and 2 mW or less, and the magnetic field modulation is set from 0.001 Tesla or more to 0.1 Tesla or less. This is because, when the microwave strength is 0.01 mW or less as shown in FIG. 13, the ESR signal is covered with the noise level whereas when the microwave strength is 2 mW or more, saturation is generated by the signal strength. Therefore the correct ESR signal is not received.

Moreover, it is further equipped with a means for calculating the accumulated electric charge carrier information which calculates the generation region of electric charge carrier, electric charge carrier type and accumulated electric charge carrier concentration from the spectral branching factor g value, line width ΔH and line shape of electron spin resonance signal obtained from electron spin resonance signal. Therefore, since the information of each electric charge carrier is calculated from the measured ESR signal, the measured results are useful for an analysis.

Figure 12:
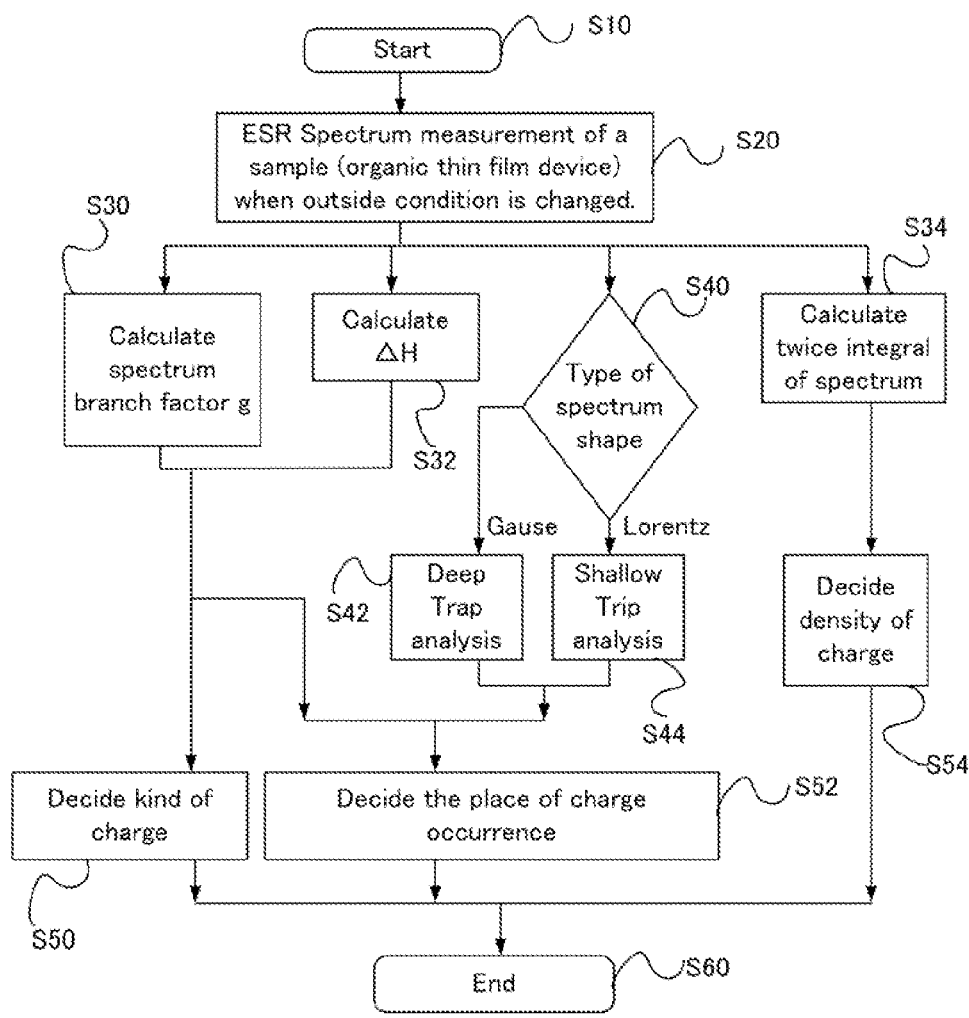
FIG. 12 is a process flow chart example calculation of the electronic states of the charge carriers for another preferred mode carrying out this invention.

FIG. 12 shows an example of the means for calculating the accumulated electric charge carrier information 420. The means for calculating the accumulated electric charge carrier information 420 can be achieved using a computer program, when the control device 400 is a computer. Note that, the control device 400 can also be a system related to digital signal processor; however, it can also be achieved using a program in that case.

As shown in FIG. 12, when the means for calculating the accumulated electric charge carrier information 420 is started, (S10), ESR spectral for the external stimuli of the sample (organic thin film element) is measured (S20). And, the spectral branching factor g value (S30) and line width ΔH are calculated (S32). Then, the spectral line shape of electron spin resonance signal is determined (S40). Further, the semi integral calculation of the spectral is carried out (S34) and electric charge carrier concentration is determined (S54). The type of the electric charge carrier is determined by using the calculated g value of spectral branching and line width ΔH (S50). In contrast, using the spectral line shape determination (S40), Deep Trap distribution is applied for Gauss type (S42) and Shallow Trap distribution is applied for Lorentz type (S44). The electric charge carrier generated region is determined by using the distribution determined as spectral branching line g value (S30) and line width ΔH (S52). Then, the program is terminated (S60).

Figure 14:
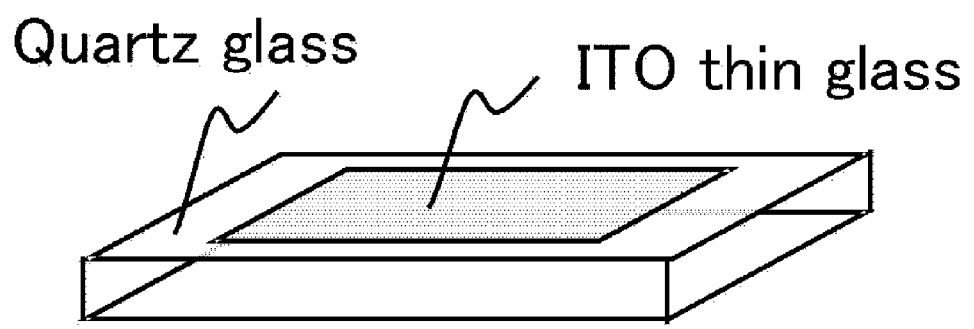
FIG. 14 is the test sample for another preferred mode carrying out this invention.
Figure 15:
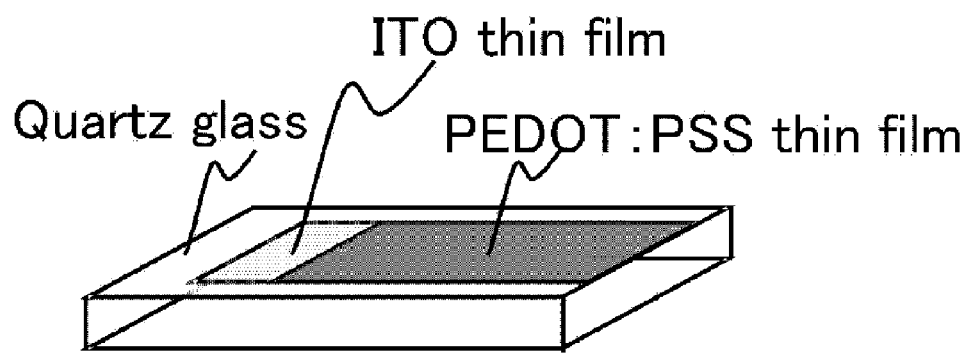
FIG. 15 is the test sample for another preferred mode carrying out this invention.
Figure 16:
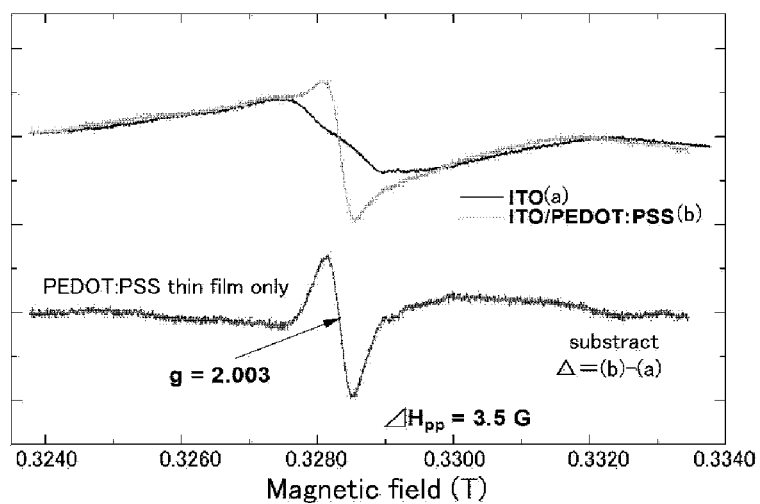
FIG. 16 is the PEDOT: PSS thin film data about the test sample for another preferred mode carrying out this invention.

As shown in FIGS. 14 to 16, two types of samples such as sample in which ITO lamella are set in fused quartz substrate (same as FIG. 14), and the sample in which ITO lamella and PEDOT: PSS lamella are set in fused quartz substrate (same as FIG. 15) are created, both are encapsulated in the sampling tube 100-2 described in FIG. 8, moved to optimum point using the means of shifting and are measured. Then the deduction of measured signals is carried out. In this manner, PEDOT: PSS thin film data to be examined can be obtained as shown in FIG. 16.

As described earlier, the electron spin measuring device of the organic thin film element of example 2 consists of some excellent functions that will be useful for a broad range of research and development. The examples of actual use are described below referring to FIG. 17 through FIG. 23 as a reference.

Figure 17:
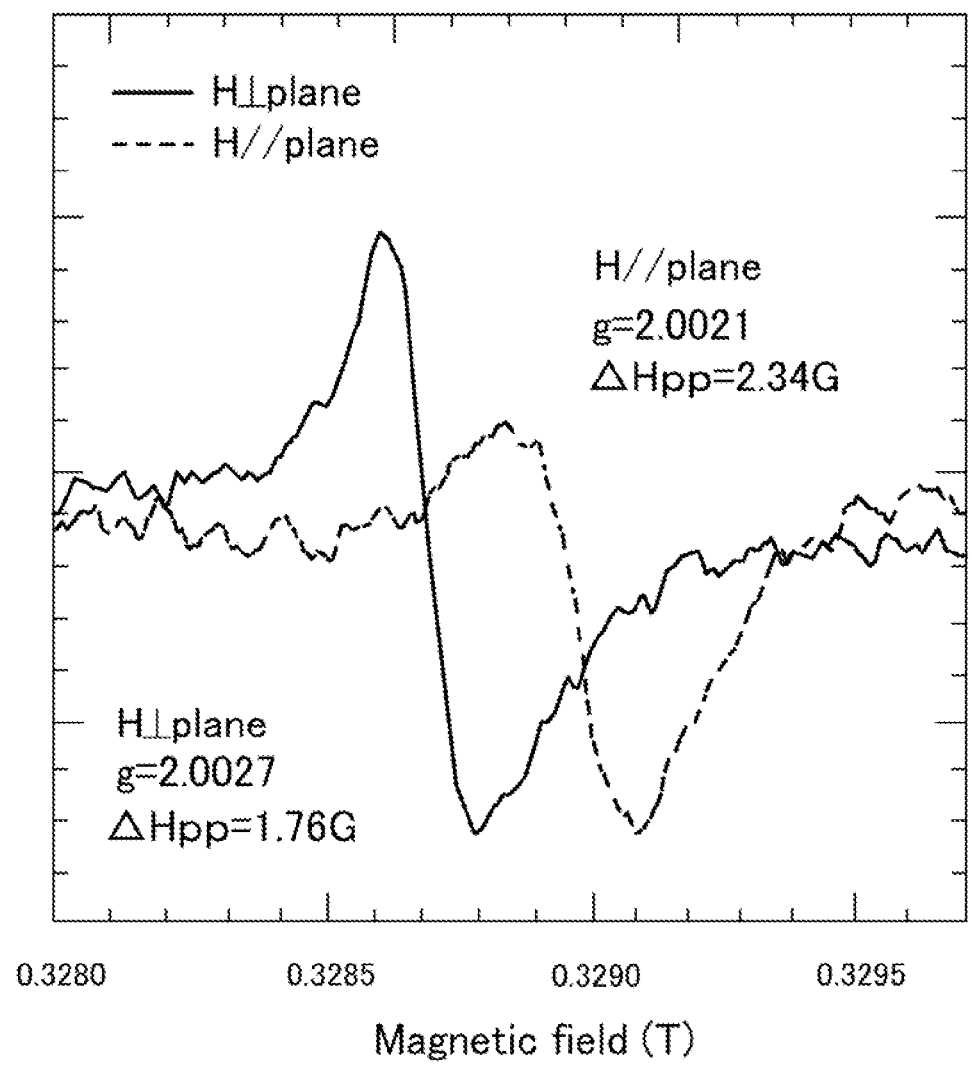
FIG. 17 is a data of ESR signal about for another preferred mode carrying out this invention.

FIG. 17 shows the anisotropic measurement results for the hetero junction type high molecular organic thin film solar battery described in FIG. 4 in terms of the magnetic field angle dependency of ESR signals. This is because the electron spin measuring device 2 of the organic thin film element can be rotated independently in a concentric fashion for the samples 120-1 and 120-2 as the point targets.

Figure 18:
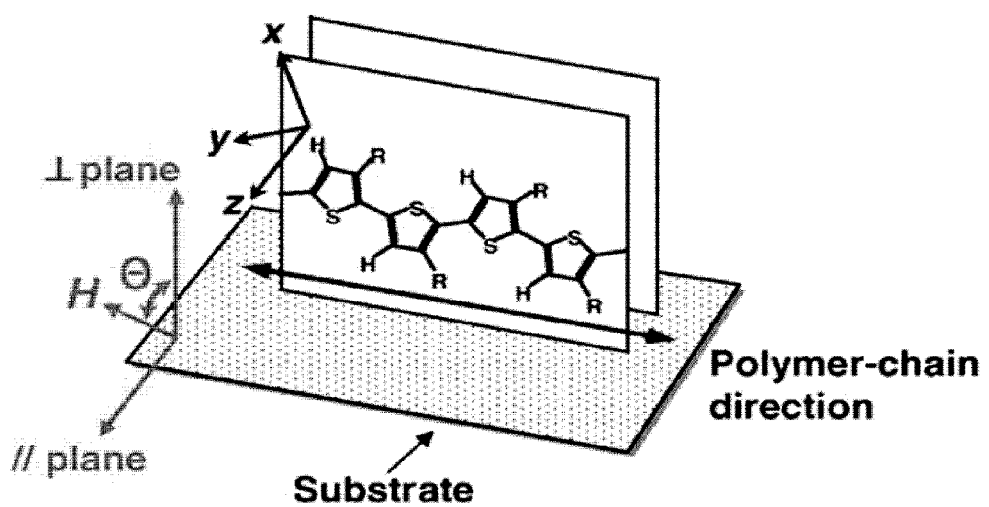
FIG. 18 is a drawing for describing the molecular aggregate structure / space expanse of the organic film elements, which became clear from the electron spin device according to another embodiment of the present invention.

As shown in FIG. 17, when the measurement of a sample, if any is carried out for the magnetic field in the right angle direction or parallel direction, it can be confirmed that the molecular orientation in the PR-P3HT of the hetero junction type high molecular organic thin film solar battery becomes the lamellar structure as shown in FIG. 18, using the magnetic field angular dependence of the value of g and the ESR signal line width.

Figure 19:
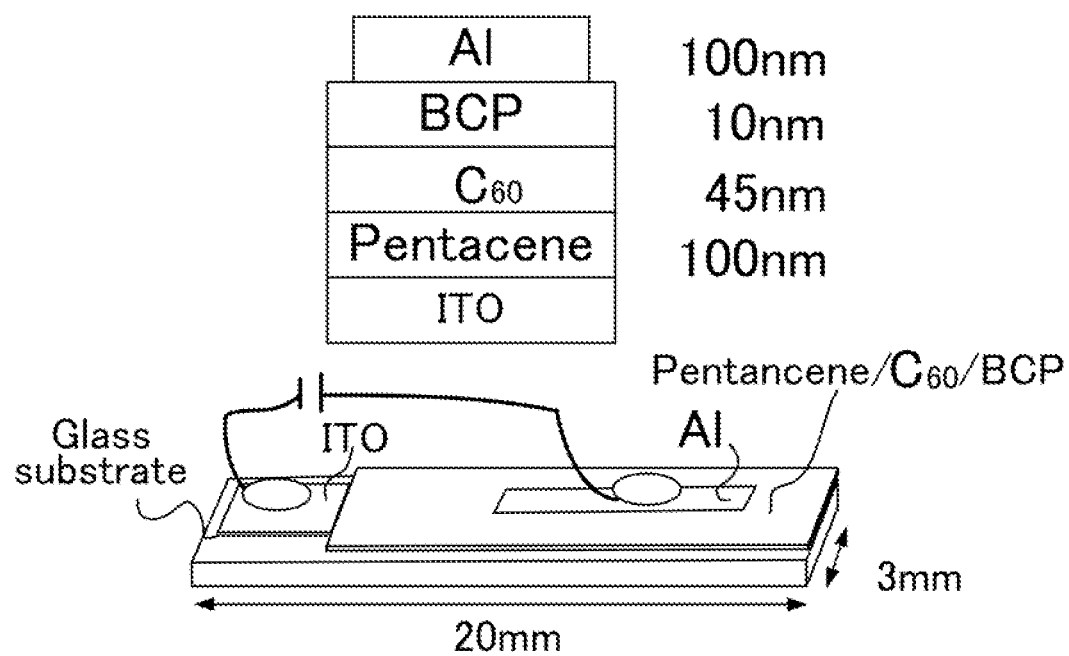
FIG. 19 is a drawing which shows a specific example of another sample 2.
Figure 20:
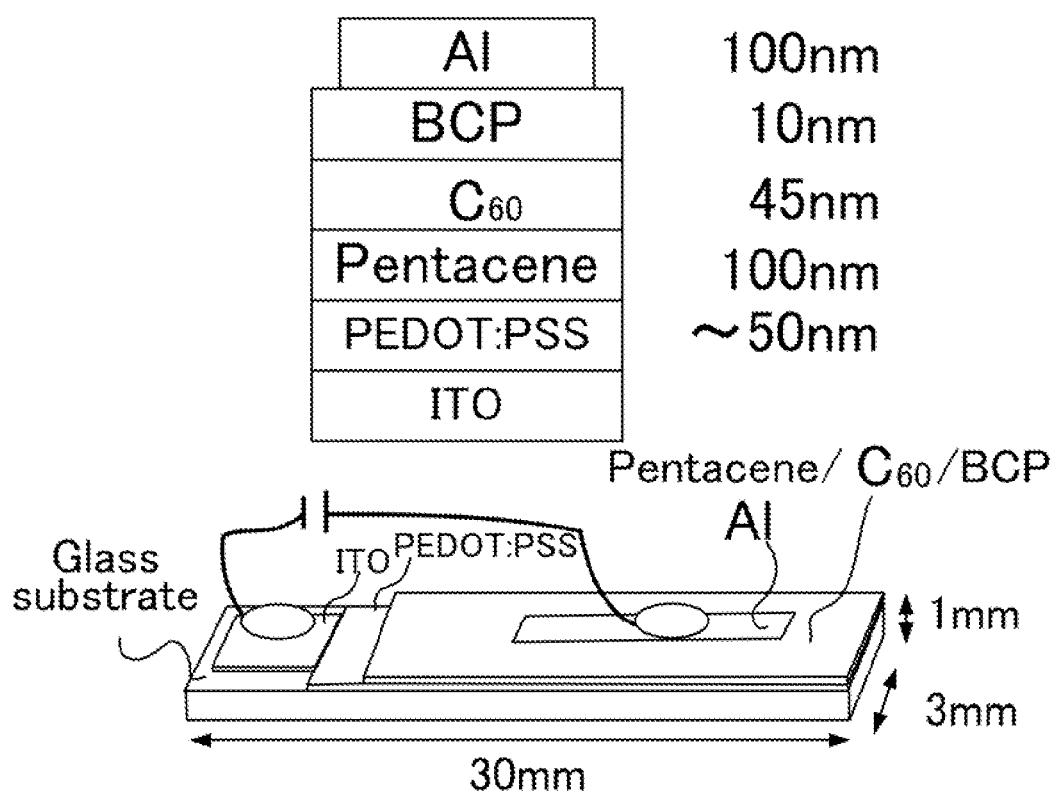
FIG. 20 is a drawing which shows a specific example of another sample 2.
Figure 22:
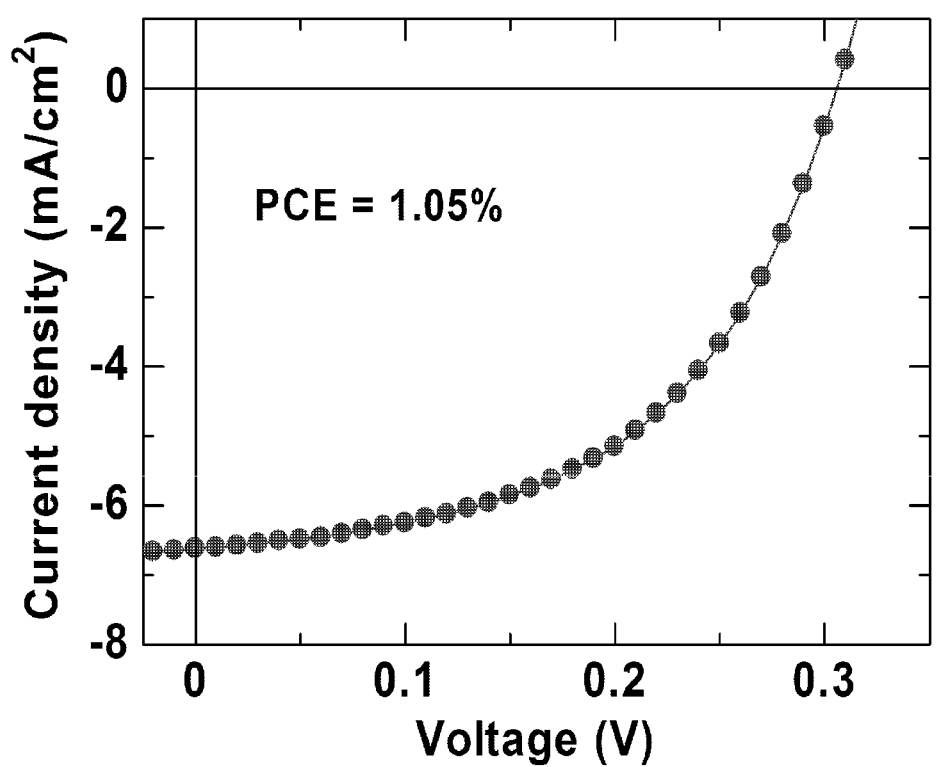
FIG. 22 is a drawing which shows the electrical characteristics of sample 2.

Next, 2 types of samples are created for the hetero junction type low molecular organic thin film solar battery as shown in FIGS. 19 and 20, and measured by using the electron spin measuring device. They are used for investigating the actual condition of the energy level of PEDOT: PSS/Pentacene/Fullerene $C_{60}$ and accumulation of the electric charge carrier. Note that the characteristics of measured thin film solar battery are shown in FIG. 22, for FIG. 20. It was found that the sample of FIG. 20 functions as a solar battery.

Figure 21:
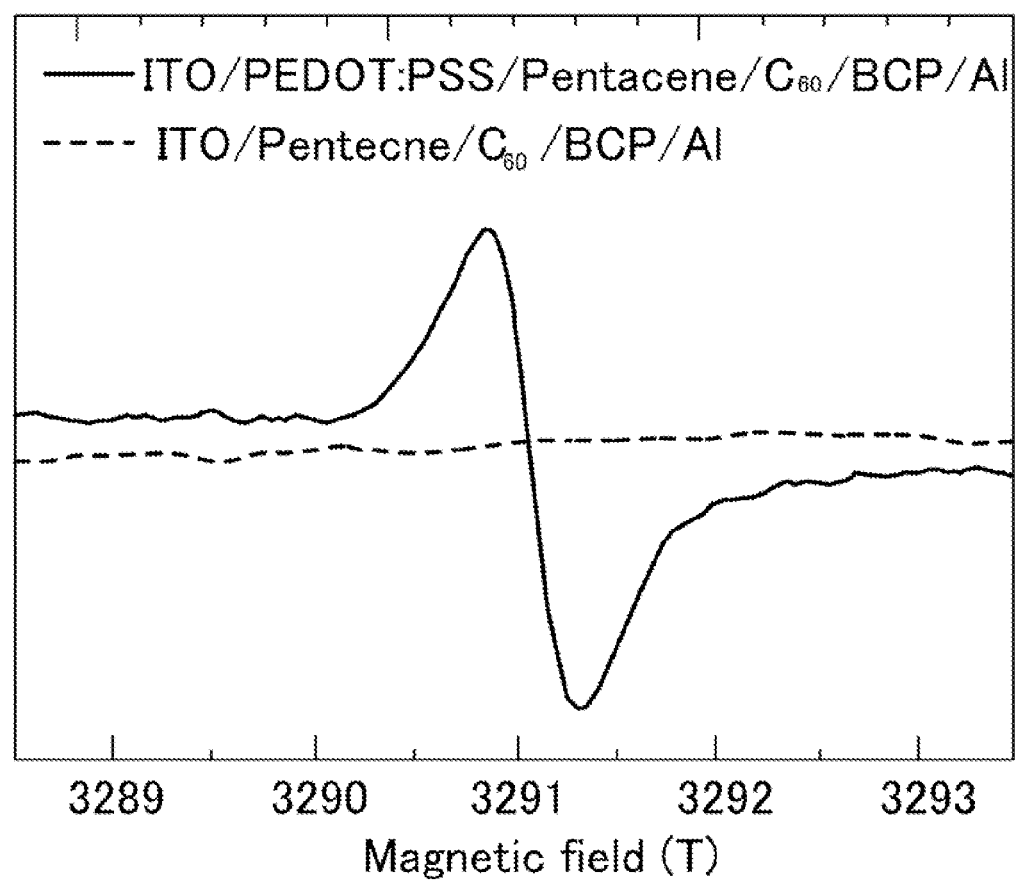
FIG. 21 is a drawing which shows the change of the ESR signal of the positive hole buffer layer dependence of the sample 2 measured by the electron spin experiment of the another embodiment of the present invention.
Figure 23:
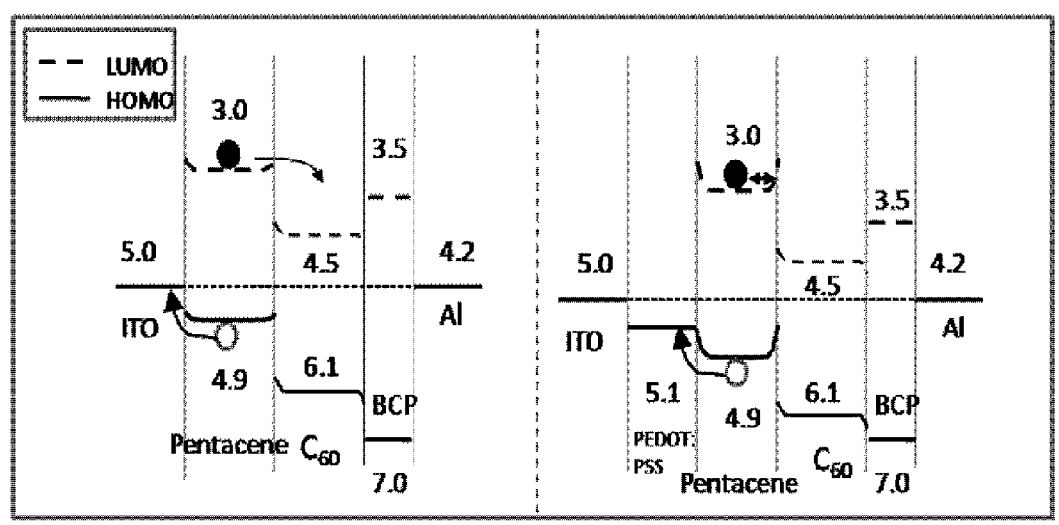
FIG. 23 is a drawing for describing the energy level and the accumulation of the electric charge carrier of the elements measured by the electron spin experiment of another embodiment of the present invention.

2 types of samples are measured using electron spin measuring device 2 and the results are shown in FIG. 21. It is determined from the data shown in FIG. 21 that energy level of the elements and the accumulation of electric charge carriers shown in FIG. 23 is the actual condition. In FIG. 23, the left side of the middle dotted line is a level diagram related to sample shown in FIG. 19 whereas the one on the right side is a level diagram related to a sample shown in FIG. 20. In other words, it was determined that the carriers are trapped only by PEDOT: PSS/Pentacene/Fullerene $C_{60}$. Note that, when light with energy even greater than the difference between HOMO (Highest Occupied Molecular Orbits 1) which is the highest energy level among the energy levels filled with organic semiconductor electrons and LUMO (Lowest Unoccupied Molecular Orbit 1) which is in the lowest orbit in the energy levels with no electrons, is illuminated, the molecule absorbs the light, free carriers are generated and the electric current starts flowing. When the molecule absorbs the light after the illumination of light, an excited exciton is formed. The exciton is a state in which the electron and holes remain connected by the Coulomb force. To start the electric current flow, the exciton reaches the PN joint interface, uses the difference between the energies of HOMO and LUMO levels of P type semiconductor organic material and N type organic semiconductor material disconnects and becomes the free carrier. Then it diffuses the electron and the hole, or moves to the internal field determined by the work function difference of the negative electrode and the positive electrode and retrieves the electric current on the outer side.

As described above, the electron spin measuring device 2 for the organic thin film element example 2 has various functions and is very useful for related research and development. Further, since the method described above can be applied, as a method of use, the explanation is omitted.

The explanation is given using the illustrative embodiment of the present invention. However, the technical scope of the present invention is not restricted to the range described in the illustrative embodiment. Various modifications and improvements can be added in the illustrative embodiment described above. An embodiment added with these modifications and improvements can be included in the technical scope of the present invention, as clear from the description of the scope of the claims.

What I claim are:

1. An electron spin measuring device of organic thin film elements, comprising:
    at least one sampling tube which a test sample is inserted into and sealed with a specified gas or in vacuum; and
    a cavity resonator into which the at least one sampling tube is inserted;
    an electrical characteristics measuring device for evaluating organic thin film elements as the test sample;
    a wire connecting the electric characteristics measuring device and the sample in the at least one sampling tube; and
    a light receiving and emitting device which irradiates light to the sample and/or detects emission from the organic thin film elements, wherein a microwave having a vibration frequency corresponding to Zeeman energy splitting produced by unpaired electron spins is irradiated in the cavity resonator, and a transition between energy levels produced upon reversing the direction of electron spin is measured; and
    a control apparatus which connects the electrical characteristics measuring device and the light receiving and emitting device by a communication line, wherein the electron spin measuring device measures the characteristic of the organic thin film elements and the characteristic of the electron spin at the same time and outputs temporal change data of the both characteristics.

2. The electron spin measuring device of the organic thin film elements according to claim 1, wherein the cavity resonator and the at least one sampling tube are respectively equipped with a means independently rotatable in a concentric fashion for the sample in the at least one sampling tube as a point target for arbitrarily varying magnetic direction and/or light illuminating direction available against a surface of the sample positioned in the at least one sampling tube.

3. The electron spin measuring device of the organic thin film elements according to claim 1, wherein the cavity resonator comprises a rotation band rotatable with the light receiving and emitting device provided on an outer circumference of the cavity resonator, and wherein the rotation band and the sampling tube respectively and independently rotates concentrically and symmetrically about a point of the sample in the sampling tube.

4. The electron spin measuring device of the organic thin film elements according to claim 3, wherein the rotation band is composed of nonmagnetic materials and equipped with a gear rotation mechanism.

5. The electron spin measuring device of the organic thin film elements according to claim 4, further comprising:
    extracting functional part electron spin resonance signal means for extracting only electron spin resonance signal in a specified functional part in comparison with a plurality of electron spin resonance signals of the samples.

6. The electron spin measuring device of the organic thin film elements according to claim 1, further comprising:
    accumulated electron charge carrier information calculating means for calculating a site producing an electric charge carrier, an electric charge type, and a concentration of stored electric carrier, from g value of spectral branching factor, a line width ΔH, and a line shape of the electron spin resonance signal which are obtained from an electron spin resonance signal.

7. A method of measuring electron spin of organic thin film elements comprising:
- providing separately on a substrate or a plurality of substrates
  - a first sample composed of organic thin film elements,
  - a second sample excluding organic functional thin films from the organic thin film elements, and
  - at least two samples including the first and second samples;
- inserting the separated samples into a sampling tube;
- sealing the sampling tube with a specified gas or in vacuum;
- inserting the sampling tube into a cavity resonator;
- irradiating a microwave having a vibration frequency corresponding to Zeeman energy splitting produced by unpaired electrons, to each of a first sample and a second sample displacing a position while sweeping a magnetic field, and at the same time, measuring a transition between energy levels produced upon reversing the direction of electron spin;
- executing a differential treatment of
  - a first electron spin resonance signal from the first sample composed of organic thin elements,
  - a second electron spin resonance signal from the second sample excluding the organic functional thin films from the organic thin film elements, and
  - a third electron spin resonance signal from a sample excluding partially the organic functional thin films from the organic thin film elements; and
- extracting only components of the electron spin resonance signals derived from the organic functional thin films.

* * * * *